(12) United States Patent
Darbyshire et al.

(10) Patent No.: US 6,953,592 B2
(45) Date of Patent: Oct. 11, 2005

(54) WATER SOLUBLE POWDERS AND TABLETS

(75) Inventors: John Darbyshire, Tolochenaz (CH); Oliver Chmiel, Orbe (CH); Johan Bernard Ubbink, Savigny (CH); Annemarie Schoonman, Montreux (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/235,671

(22) Filed: Sep. 4, 2002

(65) Prior Publication Data

US 2003/0026836 A1 Feb. 6, 2003

Related U.S. Application Data

(63) Continuation of application No. PCT/EP02/00782, filed on Jan. 25, 2002.

(30) Foreign Application Priority Data

Feb. 2, 2001 (GB) .............................................. 0102691

(51) Int. Cl.⁷ ................................................ A61K 9/14
(52) U.S. Cl. ........................ 424/489; 424/400; 424/439; 424/464; 514/23; 514/53; 514/60
(58) Field of Search ................................ 424/400, 439, 424/464, 489; 514/23, 53, 60

(56) References Cited

U.S. PATENT DOCUMENTS

| | | | |
|---|---|---|---|
| 4,746,527 A | 5/1988 | Kuypers | 426/569 |
| 4,748,040 A | 5/1988 | Kuypers | 426/569 |
| 5,039,540 A | 8/1991 | Ecanow | 426/385 |
| 5,079,018 A | 1/1992 | Ecanow | 426/385 |
| 5,271,928 A | 12/1993 | Schneider et al. | 424/9 |
| 5,298,261 A | 3/1994 | Pebley et al. | 424/488 |
| 5,380,519 A | 1/1995 | Schneider et al. | 424/9 |
| 5,382,437 A | 1/1995 | Ecanow | 424/499 |
| 5,462,759 A | 10/1995 | Westerbeek et al. | 426/568 |
| 5,531,980 A | 7/1996 | Schneider et al. | 424/9.52 |
| 5,567,414 A | 10/1996 | Schneider et al. | 424/9.52 |
| 5,643,553 A | 7/1997 | Schneider et al. | 424/9.52 |
| 5,658,551 A | 8/1997 | Schneider et al. | 424/9.51 |
| 5,911,972 A | 6/1999 | Schneider et al. | 424/9.51 |
| 6,110,443 A | 8/2000 | Schneider et al. | 424/9.51 |
| 6,136,293 A | 10/2000 | Schneider et al. | 424/9.52 |
| 6,278,616 B1 | 8/2001 | Gelsomini et al. | 361/803 |
| 2001/0008626 A1 | 7/2001 | Schneider et al. | 424/9.52 |
| 2001/0012507 A1 | 8/2001 | Schneider et al. | 424/9.52 |
| 2001/0024640 A1 | 9/2001 | Schneider et al. | 424/9.52 |
| 2002/0081738 A1 * | 6/2002 | Simonsen et al. | 435/459 |

FOREIGN PATENT DOCUMENTS

| | | |
|---|---|---|
| EP | 0 450 141 A1 | 10/1991 |
| EP | 0450 310 A1 | 10/1991 |
| EP | 0 579 328 A1 | 1/1994 |
| EP | 0 885 566 A1 | 12/1998 |
| WO | WO 98/07329 | 2/1998 |

* cited by examiner

*Primary Examiner*—Shelley A. Dodson
*Assistant Examiner*—Konata M. George
(74) *Attorney, Agent, or Firm*—Bell, Boyd & Lloyd LLC

(57) ABSTRACT

The invention relates to water soluble or water dispersible powders, tablets, or precursors therefor based on a carbohydrate matrix with improved dissolution properties in water. These components are subjected to treatment with a gas so that gas is entrapped therein, and sufficient closed porosity is provided so that gas entrapped therein promotes dissolution or dispersion upon contact with water. The powders or tablets may be pharmaceuticals or foods that optionally contain an active ingredient therein.

37 Claims, 1 Drawing Sheet

WATER SOLUBLE POWDERS AND TABLETS

CROSS-REFERENCE TO RELATED APPLICATIONS

This application is a continuation of the US national stage designation of International Application no. PCT/EP02/00782 filed Jan. 25, 2002, the content of which is expressly incorporated herein by reference thereto.

FIELD OF THE INVENTION

This invention relates to water soluble or water dispersible carbohydrate based powders and tablets that have improved reconstitution properties in water.

BACKGROUND ART

Water soluble powders and tablets based on amorphous carbohydrate matrices are used in many fields. For example, such powders or tablets in a form suitable for human consumption are used in the food, beverage, nutrition, confectionery and pharmaceutical fields. Alternatively the powders or tablets may contain materials such as detergents intended to be dissolved or dispersed in water before use. In many cases, it is desirable that the powders or tablets should dissolve or disperse rapidly on contact with water and, for example, poor tablet dissolution is known to account for many drug-bioavailability problems. The powder or tablet may contain a chemical dissolution aid and such aids are generally combinations of chemicals which are stable in solid form but which generate a gas on contact with water, for example the combination of an acid and a carbonate or bicarbonate. In some cases, the amount of the gas-generating chemicals added is such as to provide effervescent powders or tablets.

One particular type of water soluble carbohydrate powder is soluble foamer and creamer powders which upon addition of a liquid are able to provide a creamy foam and such powders have many uses. For example, they may be used to provide milk shakes or cappuccino style beverages or they may have food applications such as in desserts, soups and sauces. Soluble coffee beverage products which produce cappuccino-type beverages are particularly well known and these are usually a dry mix of a soluble coffee powder and a soluble beverage creamer. Products of this type are known which contain pockets of gas which upon dissolution of the powder produce a foam so that on the addition of water or milk (which will usually be hot), a whitened coffee beverage is produced having foam on the surface which resembles, to some extent at least, traditional Italian cappuccino. Examples of gassed soluble beverage creamers are described in EP-A-0 154 192, EP-A-0 450 310 and EP-A-0 885 566. Soluble beverage creamers which contain chemical foaming agents are also known. The formation of a foam is dependent on the powder containing an ingredient, generally a protein such as casein, which is capable of stabilizing the foam.

In many fields, the presence of gas-generating chemicals is undesirable, for example because of their effect on flavor, or they may even be prohibited. There is a need to provide water soluble or water dispersible carbohydrate based powders and tablets with improved reconstitution properties in water without the need to use such chemical dissolution aids.

SUMMARY OF THE INVENTION

According to one aspect, the present invention provides a method of increasing the solubility or dispersibility of a powder or tablet based on a carbohydrate matrix by subjecting the powder or tablet or a precursor thereof to treatment with a gas so that gas is entrapped in the powder or tablet. This method comprises providing the powder or tablet with sufficient closed porosity to retain an amount of entrapped gas therein that promotes dissolution or dispersion of the powder or tablet upon contact with water.

According to a further aspect, the present invention provides a non-foaming water soluble or water dispersible powder based on a carbohydrate matrix. This powder contains entrapped gas in an amount which is sufficient to promote dissolution or dispersion of the powder in contact with water.

According to a still further aspect, the present invention provides a water soluble or water dispersible tablet based on a carbohydrate matrix containing entrapped gas and having sufficient closed porosity to allow retention of entrapped gas in an amount which promotes dissolution or dispersion of the tablet on contact with water.

BRIEF DESCRIPTION OF THE DRAWINGS

The invention is better understood in connection with the appended drawing figures, which illustrate preferred embodiments and wherein:

FIG. 1b is a schematic representation of a granule in the tablet of FIG. 1a.

DETAILED DESCRIPTION OF THE PREFERRED EMBODIMENTS

Figure 1B:
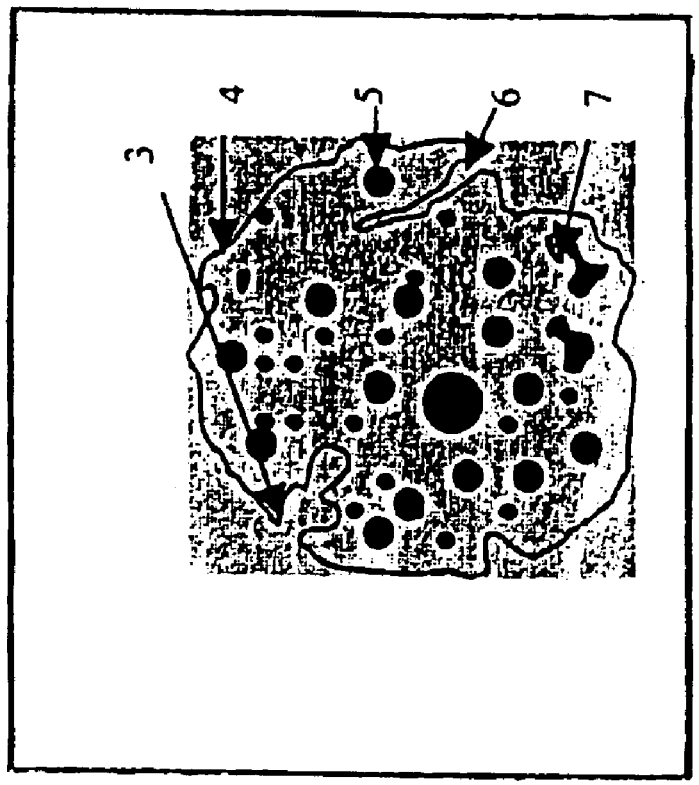

The powders and tablets with which the present invention is concerned may be based on a matrix of any suitable carbohydrate or mixture of carbohydrates. Generally, the powder or tablet includes an amorphous carbohydrate matrix which will also include other components depending on the intended use of the powder or tablet. Certain tablets may be made of the carbohydrate matrix itself, while others usually will comprise the carbohydrate matrix together with one or more other ingredients. Examples of suitable carbohydrates include sugars such as lactose, dextrose, fructose, sucrose, maltodextrin, cyclodextrins and corn syrup, starch and modified starch. If the tablets or powders are not food grade, then any other kind of water soluble or water dispersible starch can be used. The carbohydrate generally makes up at least 50% by weight of the matrix, preferably at least 75% by weight of the matrix and more preferably at least 90% by weight of the matrix.

The properties of the matrix can be influenced and, in particular optimized, by addition of plasticizers, antiplasticizers, fillers, compounds which influence the formation of crystallites or ordered regions in the material, cross-linking agents, emulsifiers, foam stabilizers, colorants or binders. Such additives are present in an amount effective to influence a matrix property, and preferably constitute from 0.5% up to no more than 25% by weight and more preferably up to no more than 10% by weight of the matrix. Tablets and powders may contain materials such as protein, hydrocolloids and fats. Tablets in particular may contain one or more active ingredients the nature of which will depend on the intended use of the tablets. Preferably, the tablets and powders contain no more than 7% by weight water, more preferably no more than 5% by weight water and most preferably no more than 3% by weight water.

Where the powder or tablet is non-foaming, the composition should either contain insufficient amounts of foam stabilizing components such as proteins to allow formation of a foam (or such components should be absent altogether), or it should contain a foam-destabilizing agent. Examples of foam destabilizing agents include isopropanol, fats and lipids, sucrose, monoesters, mono/diester mixtures and propylene glycol monostearate. In this connection, the powder or tablet should preferably be non-foaming (i.e., have no or minimal foam formation).

The powders and tablets according to the present invention include a gas entrapped therein. This may be any suitable gas which does not adversely affect the other components of the powder or tablets. Where the powder or tablets are intended for human consumption as a food, beverage, nutritional or pharmaceutical, the gas should be of food grade. Examples of suitable gases include nitrogen, carbon dioxide, air, oxygen, helium, hydrogen, argon, neon, methane, ethane, krypton, chlorine, chlorofluorocarbons or mixtures thereof. The amount of gas introduced into the powder or tablet is preferably at least 3 ml(STP)/g, more preferably at least 5 ml(STP)/g and most preferably at least 7 ml(STP)/g.

The gas may be introduced into the powder or tablet or a precursor thereof by any suitable process. One suitable technique for forming powders involves providing a matrix in the form of expanded particles and then entrapping gas in the particles. In general, the method involves heating the powder under pressure of the gas at a temperature at which the matrix softens, which may be a temperature above the glass transition point (Tg) of the matrix. Gas enters into the particles which become loaded with the gas and the particles are solidified by quenching to retain the gas in the particles. The particles containing the gas may be the final form of the product or they be admixed with a further powder form component to form the final powder product.

The expanded particles may be produced by injecting a gas into an aqueous matrix concentrate having a solids content suitable for spray drying, and this is generally above about 30% by weight. The gas may be injected into the aqueous matrix concentrate at a pressure of about 500 kPa to about 5 MPa although the pressure at which the gas is injected is generally not critical. The gassed aqueous matrix is then spray dried to a powder. The particles are then subjected to an inert gas atmosphere at high pressure and at a temperature above softening point of the matrix, which for an amorphous carbohydrate matrix may be the same as of similar to the Tg of the matrix. The pressure may be from about 100 kPa gauge to about 20 Mpa gauge. The temperature required will depend on the composition of the particles since this will influence the Tg but can readily be determined for any particle type and composition. The use of temperatures that are more than about 50° C. above the Tg of the particles is unnecessary and best avoided. The particles may be subjected to the pressure and temperature for as long as desired since increasing the time will generally increase gas entrapment but times from about 10 seconds to about 30 minutes are generally sufficient. The particles are then subjected to rapid quenching or curing to ensure entrapment of the gas. Suitable cooling procedures may be used to quench the particles.

Another suitable technique for introducing gas into particles involves injecting gas into a molten mass of the matrix for the particles which contains little or no moisture, for example in an extruder. The gas may be injected at a pressure of about 100 kPa gauge to about 20 MPa gauge. The temperature required will depend on the composition of the matrix since this will influence the melt temperature but can readily be determined for any matrix type and composition. Temperatures above about 150° C. should generally be avoided. The molten mass may then be extruded through a small orifice and comminuted into a powder. Depending on the rapidity of solidification of the matrix, the matrix may need to be cured or quenched under pressure before being formed into a powder to prevent the gas escaping from the matrix. Curing or quenching is preferably carried out rapidly and the time may vary for example from about 10 seconds to about 90 minutes.

If the final product is a powder, it may be used in the form in which it is produced by the above method or it may be mixed with other ingredients in powder form. In this case, the gas containing powder may act as a dissolution aid for the overall powder. Any active ingredients are preferably incorporated into the powder before gas loading.

Where the final product is a tablet, this may be produced in a conventional manner and subsequently loaded with gas. The process by which a particulate solid may be transformed into a tablet by the application of pressure can be divided into the two stages of consolidation and bond formation and the ability of a powder to form a tablet is dependent on a balance between the plastic deformation and the brittle fracture properties of the powder particles. Tablets may be formed by direct compression of powders and in some cases lubricants such as magnesium stearate are used to improve powder compaction. In addition, binding agents are usually applied. In the embodiments of the present invention, these binders are for example, but not exclusively, carbohydrates, starches in native or treated form, lipids, waxes and fats. Many parameters influence powder compaction including the composition, particle size, water content, compaction speed and pressure, the way in which the powder was prepared (roller dried, spray dried, freeze dried), powder flowability and powder brittleness. Further information on tablet formation can be found in standard reference works such as Pharmaceutical Powder Compaction Technology (1996) Ed Alderborn, G and Nyström, C, Marcel Dekker, New York.

According to one embodiment, foamed powders, for example foamed food powders, prepared by extruding, spray-drying or freeze-drying, and which have a high level of closed porosity, are compacted into tablets as described above and then loaded with gas by the same general method as described above for the production of powders. The holding time, for example pressurization time above Tg, plays an important role and the loading time and volume of gas entrapped depends on loading conditions and matrix composition.

It may also be possible to form pressurized powders with high closed porosity and containing a high volume of entrapped gas directly into tablets, optionally together with other ingredients. Compaction of the tablet premix must be carried out in such a way that a significant proportion of the closed porosity remains. By use of relatively low compaction pressures, most of the gas is retained in the tablet (closed pores) and it is also possible to optimize to open porosity thereby improving dissolution properties of the tablet. If the powder is softened, for example by increasing the temperature, the particles can be compacted without significant cracking thereby minimizing gas loss during compaction. Where gas containing powder is compacted with other powder form ingredients to form tablets, the gas containing component can act as a dissolution aid for the tablet as a whole.

Where carbohydrate-based tablets or powders include a gas-containing component as a dissolution aid, this component may make up 0.5 to 70% by weight of the total composition. In the final formulation, the gas-containing component generally has a softening point and/or Tg of at least 35° C., more preferably at least 45° C., and most preferably at least 55° C. In the case where the matrix is based on an amorphous carbohydrate, the softening point may be but is not exclusively restricted to the Tg.

The production of particles and tablets loaded with gas requires the gas to be transported into and entrapped by the matrix as the particles and tablets are formed. For this reason, it has been found that the mechanism of gas transport and entrapment is related to the matrix composition and, in particular, to the closed porosity of the matrix. Gas enters the matrix at temperatures above the Tg as a result of lowered matrix viscosity and increased matrix mobility. The optimum temperature range for gas to enter the matrix depends on the composition of the matrix but can readily be determined in any particular case. Below the Tg of the matrix, the rate of gas entrapment is very low and if the temperature increases too far above the Tg the matrix tends to collapse reducing gas entrapment. Within the optimum temperature range, the amount of gas entrapped increases with increased loading pressure and with increased holding time until equilibrium is reached between the pressure inside and outside the matrix.

Closed pores in the matrix are able to hold gas under pressure for prolonged periods of time and, provided that there are no cracks in the matrix, release is confined by diffusion through the glassy matrix. Good gas retention thus requires an adequate closed pore volume after loading with gas and the matrix should be resistant to cracking of the surrounding lamellae.

Non-foaming carbohydrate powders or tablets will generally contain no protein or only a small amount of protein, although if necessary a small amount of foam stabilizer can be added to obtain a powder with initial closed pores. Suitable foam stabilizers are generally proteins such as casein or whey and they may be added in an amount of, for example, from 0.1% up to 5% or 10%, but the exact level is not critical. The powder may contain any desired non-foaming ingredients such as fats and salts and active ingredients are included as appropriate depending on the intended use of the composition. Surface active ingredients besides whey proteins or sodium caseinate may be used to create initial closed pores in the powder and examples of such ingredients include saponin, surface active lipids and other proteins such as lysozyme. Porosity may also be formed by rapid quenching of gassed powders or tablets, rapid release of elevated external pressure in the softened state, or by using blowing agents, for example isobutane or halogenated chlorofluorocarbons, at elevated pressures and/or temperatures.

In one embodiment of the invention, the tablets or powder comprise a beverage base, e.g., coffee, cocoa, malt or tea. In particular, tablets comprising soluble coffee have been found to be readily dissolvable and dispersable. For example, these tablets may comprise soluble coffee, foamed powder, sugar and creamer.

Upon reconstitution of the powder or tablet, the particles containing entrapped gas will crack, break up or disintegrate, thereby increasing the specific surface area of the powder or the tablet which promotes its dispersion and subsequent dissolution.

An additional advantage of the present invention is that, if an inert gas is entrapped in the particles, its incorporation will protect any sensitive active ingredients present in the powder or tablet from interaction with atmospheric gases by saturation of the powder or tablet with the inert gas. During storage, the loss of inert gas from the direct environment of the sensitive active ingredient will be partially compensated by the very slow release of gas from the entrapment matrix. In practice, the sensitive active ingredient will often be susceptible to oxidation and a suitable inert gas for protection would be nitrogen, although other inert gases may also beneficially be used.

Examples of carbohydrate based tablets and powders according to the present invention include the following:

tablets and powders for pharmaceutical use containing gas which provide better dispersion of the drugs that they contain;

tablets and powders containing gas for food supplement applications which show better dispersion of such materials as enzymes, probiotic bacteria and vitamins;

tablets and powders containing gas for food application, for example instant food powders;

tablets containing gas in the form of bonbons, for example for the confectionery field, tablets and powders for infant nutrition and tablets for the culinary field such as bouillon cubes;

cleaning tablets or powders such as tablets containing agents to clean contact lenses;

tablets or chewing gums for cleaning teeth upon wetting/chewing in the mouth where dissolution speed may affect uptake of sodium fluoride in the mouth;

tablets or powders for animal consumption, for example pet foods containing gas, flavors and nutritional ingredients, for example vitamins or probiotic microorganisms and their metabolites;

tablets and powders containing agrochemical ingredients for example fertilizers, pesticides or herbicides;

tablets and powders containing cosmetic ingredients, for example bath and shower preparations.

It is understood that this technology would also be applicable to other fields such as household products.

EXAMPLES

The invention is illustrated by the following examples of the most preferred embodiments.

Example 1

Preparation of Tablets and Powders

Tablets were prepared from freeze-dried amorphous powders (particle size between 0.4 and 0.9 mm) consisting of maltodextrin DE 12 (Sugro, AG Switzerland) with varying percentage of sodium caseinate (Santis, AG, Switzerland) (Table 1). The tablets (diameter 38 mm, height 2 mm) were compressed with an estimated tabletting pressure of 260 MPa using a standard workshop press (PRM 60 PHP, Rassant, France).

TABLE 1

| Composition of samples used for tablet compression | | |
|---|---|---|
| Sample | Maltodextrin DE 12 (wt. %) | Sodium caseinate (wt. %) |
| 1 | 90 | 10 |
| 2 | 80 | 20 |
| 3 | 70 | 30 |

Example 2

Gas Loading

The procedure for loading the samples with nitrogen gas is as follows. First, the samples are pressurized with nitrogen gas at room temperature in a closed batch autoclave (volume 5 liter, type DN 2000 (Meili S. A, Switzerland), maximum pressure 30 bar). The autoclave is equipped with a temperature sensor (PT-100, no. AC 1912, Rotronic, Switzerland), relative humidity sensor (HP 101 A-L5-ES 1W, Rotronic, Switzerland), pressure sensor (ED 510/354.461/105, Haenni, Switzerland) and mixer (UFM1-F, SAIA). Second, the powder is heated under pressure to temperatures above its glass transition temperature. Above the Tg, the gas is readily taken up by the sample. The gas is retained in the sample by relieving the pressure in the vessel only after cooling the powder to temperatures below its glass transition temperature. The total amount of gas absorbed can by varied by varying the loading temperature, pressure and time above Tg.

Example 3

Tablets

Figure 1A:
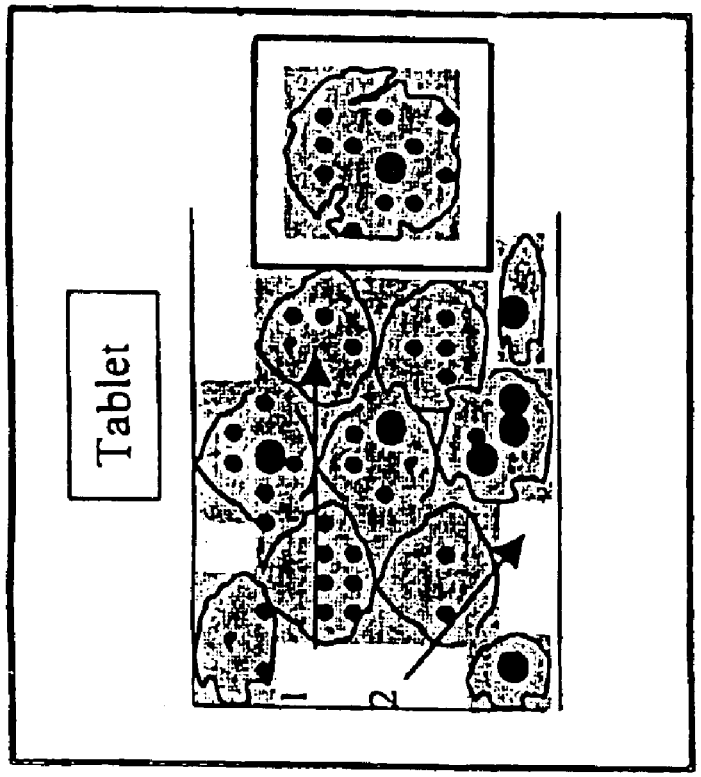
FIG. 1a is a schematic representation of a tablet according to the invention.

A powder sample 3 with Aw 0.32 (see Example 1 above) is light compressed (compaction pressure ~20 kPa) and loaded in an autoclave according to method described above. The compaction pressure is much lower than the compaction pressure normally used for the production of tablets. By lowering the compaction pressure, tablets with higher closed and open porosity can be obtained. In this connection, reference is made to FIGS. 1a and 1b which represent the tablet (FIG. 1a) and the granule in the tablet (FIG. 1b). In these figures, the legends are as follows:

1=solid matrix: matrix excluding both open and closed pores
2=voids: space or interstice between particles
3=open pore: cavity or channel communicating with the surface of the solid
4=micropore: pore <20 Å
5=closed pore: cavity not communicating with the surface
6=crack: volume of thin fractures inside the solid matrix
7=connected pore: pore in connection with another pore or void volume The loading pressure was 50 bar, loading time 60 min. and loading temperature 90° C. The density of the tablet for gas loading is 1.3532 g/cm³ and after gas loading 1.3069 g/cm³. After gas loading a closed porosity of 13% is measured, an open porosity of 58% and the tablet contains 5.3 ml/g gas, showing improved dissolution.

Example 4

Powder

Powder sample 2 with an Aw 0.23 is pressurized in an autoclave according to method described above. Pressure 50 bar, holding time 1 hour, temperature 120° C. The powder contains after gassing a closed porosity of 52%, density 0.73 g/cm³ and 25 ml gas/gram. Upon reconstitution this powder dissolves very fast.

Example 5

Beverage Tablets

Tablets where compacted from the following two premixes:

| Sample | Soluble coffee[1] (wt. %) | Foamed powder[2] (wt. %) | Sucrose[3] (wt. %) | Creamer[4] (wt. %) |
|---|---|---|---|---|
| 1 | 67 | — | 33 | — |
| 2 | 15 | 25 | — | 60 |

[1]Spray-dried soluble coffee powder.
[2]Foamed carbohydrate powder (diary based).
[3]Crystalline sucrose.
[4]Spray-dried creamer powder.

Tablets (diameter 2 cm, thickness about 7 mm, tablet weight about 4 g) were compacted at low to medium compaction pressure using a manual tablet press. Samples where loaded with nitrogen after compaction. The loading conditions where 90 bar and 95° C. The loading time was 30 minutes. Afterwards, dissolution tests where carried out in water of about 70° C. The gas-loaded tablets dissolved noticeably more rapidly than the ones which were not loaded with gas. The sample containing the creamer also formed some foam on top of the beverage.

What is claimed is:

1. A method of increasing the solubility or dispersibility of a carbohydrate-based matrix which comprises subjecting a carbohydrate to treatment with a gas so that gas is entrapped therein and providing the carbohydrate with sufficient closed porosity to retain an amount of entrapped gas therein that promotes dissolution or dispersion of the carbohydrate-based matrix upon contact with water.

2. The method according to claim 1, wherein the carbohydrate matrix comprises an amorphous carbohydrate.

3. The method according to claim 1, wherein the carbohydrate matrix comprises sugar, starch or modified starch.

4. The method according to claim 1, wherein the carbohydrate matrix includes at least 50% by weight of carbohydrate(s) therein.

5. The method according to claim 1, wherein the carbohydrate is present in the matrix in an amount of at least 75 to 90% by weight.

6. The method according to claim 1, wherein the matrix also contains one or more of a protein, a hydrocolloid or a fat.

7. The method according to claim 1, wherein the matrix is non-foaming.

8. The method according to claim 7, wherein the matrix contains a foam-destabilizing agent and less than 5% by weight foaming protein.

9. The method according to claim 1, wherein the gas that is entrapped in the matrix is nitrogen, carbon dioxide, air, oxygen, helium, hydrogen, argon, neon, methane, ethane, krypton, chlorine, a chlorofluorocarbon or a mixture thereof.

10. The method according to claim 1, wherein the matrix contains therein at least 3 ml (STP)/g of gas.

11. The method according to claim 1, wherein the matrix contains at least 5 to 7 ml (STP)/g of gas.

12. The method according to claim 1, wherein the matrix is formed as a powder, with the gas entrapped in the carbohydrate in the form of expanded particles.

13. The method according to claim 12, wherein the gas is introduced into the particles by subjecting the particles to an atmosphere of the gas under pressure at a temperature that is higher than the softening point of the carbohydrate matrix.

14. The method according to claim 12, which further comprises forming tablets from the expanded particles.

15. The method according to claim 1, which further comprises forming tablets from particles that include the carbohydrate and entrapping gas in the carbohydrate particles.

16. The method according to claim 15, wherein the gas is introduced into the tablets by subjecting the tablets to an atmosphere of the gas under pressure at a temperature above the Tg of the carbohydrate.

17. The method according to claim 15, wherein the matrix is present in a pharmaceutical or a food, and optionally contains one or more active ingredients.

18. A non-foaming, water-soluble or water-dispersible carbohydrate-based matrix containing entrapped gas in closed pores in an amount which is sufficient to promote dissolution or dispersion of the matrix upon contact with water.

19. The carbohydrate-based matrix according to claim 18, wherein the carbohydrate comprises an amorphous carbohydrate.

20. The carbohydrate-based matrix according to claim 18, wherein the carbohydrate matrix comprises sugar, starch or modified starch.

21. The carbohydrate-based matrix according to claim 18, wherein the carbohydrate matrix comprises at least 50% by weight of carbohydrate(s).

22. The carbohydrate-based matrix according to claim 21, wherein the carbohydrate comprises at least 75% to 90% by weight of the matrix.

23. The carbohydrate-based matrix according to claim 18, which contains a foam-destabilizing agent and less than 5% by weight foaming protein.

24. The carbohydrate-based matrix according to claim 18, wherein the entrapped gas is nitrogen, carbon dioxide, air, oxygen, helium, hydrogen, argon, neon, methane, ethane, krypton, chlorine, a chlorofluorocarbon or a mixture thereof.

25. The carbohydrate-based matrix according to claim 18, which contains at least 3 ml (STP)/g of gas.

26. The carbohydrate-based matrix according to claim 18, which contains at least 5 to 7 ml (STP)/g of gas.

27. The carbohydrate-based matrix according to claim 18, which is a pharmaceutical or a food and optionally contains an active ingredient.

28. The carbohydrate-based matrix according to claim 18, in powder form.

29. The carbohydrate-based matrix according to claim 18, in tablet form.

30. A method for the production of a carbohydrate-based matrix that dissolves or becomes dispersed upon contact with water, which comprises subjecting a carbohydrate to treatment with a gas so that gas is entrapped therein and providing the carbohydrate with sufficient closed porosity to retain an amount of entrapped gas therein that promotes dissolution or dispersion of the carbohydrate-based matrix upon contact with water.

31. The method according to claim 30, which further comprises forming expanded particles of the carbohydrate and entrapping gas in the expanded particles.

32. The method according to claim 31, wherein the gas is introduced into the expanded particles by subjecting the particles to an atmosphere of the gas under pressure at a temperature above the softening point of the carbohydrate matrix or above the Tg of the carbohydrate.

33. The method according to claim 31, wherein the matrix is formed as a powder, with the gas entrapped in the expanded particles of the carbohydrate.

34. The method according to claim 30, which further comprises forming tablets from particles that include the carbohydrate and entrapping gas in the carbohydrate particles.

35. A water-soluble or water-dispersible carbohydrate-based matrix made by the process of claim 30.

36. Water-soluble or water-dispersible carbohydrate-based powder made by the process of claim 33.

37. Water-soluble or water-dispersible carbohydrate-based tablets made by the process of claim 34.

\* \* \* \* \*